(12) United States Patent
Konishi et al.

(10) Patent No.: US 7,947,859 B2
(45) Date of Patent: May 24, 2011

(54) PROCESS FOR PRODUCTION OF CYCLOOLEFIN

(75) Inventors: Mitsuo Konishi, Chiyoda-ku (JP); Teruhiko Inoue, Chiyoda-ku (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 702 days.

(21) Appl. No.: 11/912,575

(22) PCT Filed: Aug. 18, 2006

(86) PCT No.: PCT/JP2006/316235
§ 371 (c)(1),
(2), (4) Date: Oct. 25, 2007

(87) PCT Pub. No.: WO2007/023739
PCT Pub. Date: Mar. 1, 2007

(65) Prior Publication Data
US 2009/0048425 A1    Feb. 19, 2009

(30) Foreign Application Priority Data

Aug. 26, 2005  (JP) .................. 2005-245292

(51) Int. Cl.
*C07C 5/11* (2006.01)
*C07C 5/10* (2006.01)

(52) U.S. Cl. ........ 585/273; 585/271; 585/269; 585/266; 585/277; 502/327; 502/326

(58) Field of Classification Search ............ 502/327, 502/326, 217, 223, 261; 585/269, 273, 277
See application file for complete search history.

(56) References Cited

U.S. PATENT DOCUMENTS

| | | | | |
|---|---|---|---|---|
| 4,444,727 A | * | 4/1984 | Yanagihara et al. | 422/223 |
| 4,734,536 A | | 3/1988 | Nagahara et al. | |
| 5,157,179 A | | 10/1992 | Setoyama et al. | |
| 5,569,803 A | * | 10/1996 | Takewaki et al. | 585/269 |
| 5,935,441 A | * | 8/1999 | O'Neill et al. | 210/638 |
| 6,060,423 A | | 5/2000 | Chen et al. | |
| 6,077,983 A | * | 6/2000 | Ono et al. | 585/269 |
| 7,388,119 B2 | * | 6/2008 | Bottcher et al. | 585/379 |
| 7,618,917 B2 | * | 11/2009 | Vanoppen et al. | 502/326 |
| 2004/0176549 A1 | * | 9/2004 | Bottcher et al. | 525/507 |

FOREIGN PATENT DOCUMENTS

| | | |
|---|---|---|
| CN | 499322 | 8/1991 |
| CN | 85112910 | 10/1996 |
| CN | 87116190 | 9/1998 |
| CN | 1249291 A | 4/2000 |
| CN | 403676 | 9/2000 |
| CN | 460435 | 10/2001 |
| DE | 198 45 283 A1 | 4/2000 |
| EP | 0 220 525 A1 | 5/1987 |
| JP | 2-19096 | 4/1990 |
| JP | 3-41216 | 6/1991 |
| JP | 5-12331 | 2/1993 |
| JP | 7-39353 | 5/1995 |
| JP | 8-19012 | 2/1996 |
| JP | 8-25919 | 3/1996 |
| JP | 8-253433 | 10/1996 |
| JP | 8-259473 | 10/1996 |
| JP | 8-325172 | 12/1996 |
| JP | 08-325172 A | * 12/1996 |
| JP | 2634828 | 4/1997 |
| JP | 10-330294 | 12/1998 |
| JP | 2886563 | 2/1999 |
| JP | 3125913 | 11/2000 |
| JP | 2001-26556 | 1/2001 |
| WO | 97/16249 | 9/1997 |

OTHER PUBLICATIONS

Aldrich Catalogue (1994-1995), p. 134.*
Mieth et al., "The Effect of Catalyst Preparation on the Performance of Alumina-Supported Ruthenium Catalysts. II. The Impact of Residual Chloride" *Journal of Catalysis*, vol. 118, p. 218-226, 1989.
Supplementary European Search Report dated Nov. 30, 2009 that issued with respect to patent family member European Patent Application No. 06796546.7.
English Language abstract of JP 8-325172.
English Language abstract of JP 8-253433.
T. Asaoka, Oyo Shogaku Sankyo, Sankyo Publishing Co., Ltd., 1969, pp. 62-63; accompanied by an English language translation.
English Language abstract of JP 8-25919.
English Language abstract of JP 5-12331.
English Language abstract of JP 8-19012.
English Language abstract of JP 2-19096.
English Language abstract of JP 7-39353.
English Language abstract of JP 3-41216.

(Continued)

*Primary Examiner* — Rip A. Lee
(74) *Attorney, Agent, or Firm* — Greenblum & Bernstein, PLC

(57) ABSTRACT

According to the present invention, when cycloolefins are produced by partially hydrogenating a monocyclic aromatic hydrocarbon with hydrogen in the presence of a ruthenium catalyst, water, and a metal sulfate, the decrease in catalytic activity and cycloolefin selectivity is suppressed by reducing the concentration of chloride ions dissolved in the water in which the catalyst is present to 300 wt ppm or less and regenerating a part or all of the catalyst for reuse. Zinc sulfate is preferably used as the metal sulfate. Further, the raw materials and catalyst to be supplied to the reaction preferably have a reduced chloride ion content. This method can suppress the decrease in long-term catalytic activity and cycloolefin selectivity. Furthermore, the catalytic activity and cycloolefin selectivity after catalyst regeneration can be maintained at a high level. As a result, cycloolefins can be efficiently produced for a long period of time.

6 Claims, No Drawings

OTHER PUBLICATIONS

English Language abstract of JP 2634828.
English Language abstract of JP 2886563.
English Language abstract of WO 97/16249.
English Language abstract of JP 2001-26556.
English Language abstract of JP 10-330294.
English Language abstract of JP 3125913.
English Language abstract of JP 8-259473.
Mazzieri et al., "XPS, FTIR and TPR characterization of $Ru/Al_2O_3$ catalysts," *Applied Surface Science*, vol. 210, pp. 222-230, 2003.
Chinese Office Action issued with respect to Chinese Patent Application No. 200680021304.X, dated Aug. 26, 2010, along with an English language translation thereof.
English language Abstract of TW 88101951.

* cited by examiner

PROCESS FOR PRODUCTION OF CYCLOOLEFIN

TECHNICAL FIELD

The present invention relates to a method for producing a cycloolefin by hydrogenating a monocyclic aromatic hydrocarbon in the presence of a ruthenium catalyst. Cycloolefins, particularly cyclohexenes, have great value as intermediate raw materials for industrial organic chemical products, and are useful particularly as raw materials for polyamides, lysine, and the like.

BACKGROUND ART

Various methods are known as a method for producing cycloolefins. Among others, a method for partially hydrogenating a monocyclic aromatic hydrocarbon using a ruthenium catalyst is most typical. Many results of the investigation on catalyst components, types of carriers, metal salts as additives to the reaction system, or the like are reported as a method for increasing yield (conversion×selectivity).

For a reaction system containing both water and zinc which gives a relatively high yield of cycloolefin, there are proposed several methods including (1) a method in which a catalyst prepared by loading particles mainly composed of metallic ruthenium having an average crystallite size of 3 to 20 nm on a carrier is used as a catalyst for partially reducing monocyclic aromatic hydrocarbons with hydrogen in the presence of both water and at least one zinc compound under a neutral or acidic condition (Patent Document 1); (2) a method in which all of at least one of a zinc oxide and a zinc hydroxide in an amount of the saturated solubility thereof or less is present in a dissolved state for producing cycloolefins by partially hydrogenating monocyclic aromatic hydrocarbons in the presence of a ruthenium catalyst (Patent Document 2); (3) a method in which hydrogenation catalyst particles having an average crystallite size of 20 nm or less mainly composed of metallic ruthenium are used for partially reducing monocyclic aromatic hydrocarbons by hydrogen in the presence of water, the reaction being carried out in the presence of at least one solid basic zinc salt under a neutral or acidic condition (Patent Document 3); and the like.

When a method for producing cycloolefins by partially hydrogenating monocyclic aromatic hydrocarbons with hydrogen using a ruthenium catalyst is industrially carried out, the catalyst can be preferably used for a long period of time so as to reduce the frequency of replacing the catalyst, which will inhibit efficient production if it is high. However, it is known that when the catalyst is used for a long period of time, the activity of the catalyst decreases. A decrease in activity of the catalyst caused by a physical change (e.g., sintering) of the active site of the catalyst itself due to reaction circumstances (temperature and reaction heat), caused by the accumulation of a catalytic poison (e.g., a sulfur compound or a foreign metal), caused by the assumed interaction between hydrogen and ruthenium, or the like is reported.

For example, Patent Document 4 describes an example of poisoning by a sulfur compound, and Patent Document 5 describes an example of poisoning by iron. Further, Patent Document 6 discloses an example of a method for regenerating a ruthenium catalyst poisoned by a sulfur compound.

As a method for regenerating the ruthenium catalyst whose activity has decreased due to the interaction between hydrogen and the ruthenium catalyst, there are proposed a method of bringing the ruthenium catalyst into contact with oxygen in a liquid phase (Patent Document 7); a method of maintaining the catalyst at a hydrogen partial pressure lower than that at the hydrogenation and at a temperature not lower than the temperature lower by 50° C. than the hydrogenation temperature (Patent Document 8); a method comprising the steps of bringing the ruthenium catalyst into contact with oxygen in a liquid phase and maintaining the catalyst at a hydrogen partial pressure lower than that at the hydrogenation and at a temperature not lower than a the temperature lower by 50° C. than the hydrogenation temperature (Patent Document 9); and the like. Furthermore, in Patent Document 10, a method and an apparatus are proposed in which a part of the catalyst in continuous reaction is continuously or intermittently taken out the reactor for carrying out regeneration treatment and returned again to the reactor for carrying out partial hydrogenation.

In addition, it is also known that when the catalyst is used for a long period of time, the selectivity of cycloolefins varies with time. For the purpose of avoiding the variation of the selectivity, there have been proposed a method in which the reaction is carried out while changing the concentration of a metal sulfate in the water phase (Patent Document 10), a method in which sulfuric acid is added to the reaction system (Patent Document 11), and the like.

On the other hand, Patent Document 12 describes a method for producing cycloolefins using a catalyst prepared by adjusting the chloride ion concentration in the catalyst to 400 wt ppm or less based on 1 part by weight of ruthenium and then bringing the catalyst into contact with hydrogen. This document describes that a chloride as well as a nitrate, a sulfate, an acetate, a phosphate, and the like of a metal such as zinc, manganese, and cobalt can also be used as a metal salt that can be contained in water during reaction.

Further, Patent Document 13 describes a method for producing cycloolefins using water having an electric conductivity of 1 µS/cm or less. Similar to Patent Document 11, this document describes that a chloride as well as a nitrate, a sulfate, an acetate, a phosphate, and the like of a metal such as zinc, manganese, and cobalt can also be used as a metal salt that can be contained in the water phase during reaction.

However, in all of the above-described methods, there remains a problem that a long-term use of the catalyst may cause the physical change of the active site of the ruthenium catalyst itself, leading to the decrease in the selectivity of cycloolefins. Investigations by the present inventors have revealed that the presence of chloride ions in the reaction system not only causes decrease in the catalytic performance but also leads to a problem that the regeneration treatment of the catalyst cannot restore the activity thereof. None of the above-described documents mention anything about the influence of chloride ions present in the reaction system on the catalytic performance.

Patent Document 1: JP-B-8-25919
Patent Document 2: JP-B-5-12331
Patent Document 3: JP-B-8-19012
Patent Document 4: JP-B-2-19096
Patent Document 5: JP-B-7-39353
Patent Document 6: JP-B-3-41216
Patent Document 7: JP-B-2634828
Patent Document 8: JP-B-2886563
Patent Document 9: WO 97/16249
Patent Document 10: JP-A-2001-26556
Patent Document 11: JP-A-10-330294
Patent Document 12: JP-B-3125913
Patent Document 13: JP-A-8-259473

None of the above-described prior documents mention how to solve the problem of the decrease in the activity of the ruthenium catalyst due to the physical change (e.g., sintering)

of the active site of the ruthenium catalyst itself by a long-term use of the catalyst and describe the influence of the change of the active site on the change of the conversion or selectivity of cycloolefins.

It is an object of the present invention to provide a method for suppressing physical change occurring in the active site of a ruthenium catalyst when the ruthenium catalyst is used for a long period of time, in particular, a method capable of suppressing the decrease in the activity and cycloolefin selectivity after the catalyst is subjected to a known catalyst regeneration treatment.

DISCLOSURE OF THE INVENTION

The present inventors have intensively investigated the influence of the amount of chloride ions in water when a ruthenium catalyst is used for a long period of time on the activity and selectivity of the catalyst from the viewpoint as described above. As a result, the inventors have surprisingly found that the chloride ion concentration in water affects the physical change of the ruthenium catalyst. In addition, the inventors have also found that this physical change affects the regeneration capability of the catalyst. As a result, the inventors have found that the decrease in the activity and selectivity of the catalyst can be significantly suppressed by producing cycloolefins in the state where the chloride ion concentration is kept at a low level and by subjecting the catalyst to a known catalyst regeneration method, and thus have achieved the present invention.

The present invention comprises the followings:
(1) A method for producing a cycloolefin by partially hydrogenating a monocyclic aromatic hydrocarbon with hydrogen in the presence of a ruthenium catalyst, water, and a metal sulfate, characterized in that chloride ions dissolved in the water in which the catalyst is present have a concentration of 300 wt ppm or less; the method comprises a step for regenerating a part or all of the catalyst; and the catalyst is reused.
(2) The method for producing a cycloolefin according to the above-described (1), characterized in that the concentration of chloride ions dissolved in the water in which the catalyst is present is 200 wt ppm or less.
(3) The method for producing a cycloolefin according to the above-described (1), characterized in that the metal sulfate comprises zinc sulfate.
(4) The method for producing a cycloolefin according to the above-described (1), characterized in that the ruthenium catalyst is a catalyst comprising a carrier and/or a dispersant, and the concentration of chloride ions contained in the carrier and/or the dispersant is 200 wt ppm or less.
(5) The method for producing a cycloolefin according to the above-described (1), characterized in that the ruthenium catalyst comprises zirconium oxide as a carrier and/or a dispersant, and the concentration of chloride ions contained in the zirconium oxide is 100 wt ppm or less.
(6) The method for producing a cycloolefin according to the above-described (1), characterized in that the concentration of chloride ions contained in the monocyclic aromatic hydrocarbon is 10 wt ppm or less.
(7) The method for producing a cycloolefin according to the above-described (1), characterized in that the concentration of chloride ions contained in the hydrogen is 1 mg-Cl/Nm$^3$-H$_2$ or less (wherein N (normal) means that the unit is based on the gas in the standard state).
(8) The method for producing a cycloolefin according to the above-described (1), characterized in that the concentration of chloride ions contained in the water provided for the partial hydrogenation is 20 wt ppm or less.
(9) The method for producing a cycloolefin according to the above-described (1), characterized in that the concentration of chloride ions in the catalyst is 400 wt ppm or less.

ADVANTAGES OF THE INVENTION

According to the present invention, a long-term catalytic activity and cycloolefin selectivity can be maintained, and the catalytic activity and cycloolefin selectivity after the catalyst is regenerated are also high. Because of less frequency of complicated operations such as the replacement of a catalyst or the addition of an unused catalyst, cycloolefins can be efficiently produced for a long period of time while suppressing the decrease in cycloolefin selectivity, in the long-term production of cycloolefins.

BEST MODE FOR CARRYING OUT THE INVENTION

The present invention will now be described in detail below.

Monocyclic aromatic hydrocarbons used in the present invention may include benzene and a benzene substituted with a lower alkyl group having from 1 to 4 carbon atoms such as toluene and xylene.

The hydrogen pressure for the partial hydrogenation with hydrogen according to the present invention is generally from 1 to 20 MPa, preferably from 2 to 7 MPa. When the hydrogen pressure is too low, the cycloolefin selectivity decreases, and when the hydrogen pressure is too high, the hydrogen or the monocyclic aromatic hydrocarbons must be supplied to the reactor at a high pressure. Both cases are inefficient. The temperature during reaction is generally from 50 to 250° C., preferably from 100 to 200° C. When the reaction temperature is too low, the reaction rate decreases, and a too high reaction temperature may promote the growth (sintering) of the average crystallite size of ruthenium, the catalyst, resulting in the rapid decrease in the catalytic activity.

The ruthenium catalyst used in the present invention is preferably the one which contains metallic ruthenium obtained by previously reducing various ruthenium compounds. Examples of the ruthenium compounds which can be used in the present invention include halides such as chlorides, bromides and iodides, nitrates, sulfates, hydroxides, various complexes containing ruthenium such as a ruthenium carbonyl complex, a ruthenium acetylacetonato complex, a ruthenocene complex, a ruthenium amine complex and a ruthenium hydride complex, and compounds derived from these complexes. These ruthenium compounds can be used in combination of two or more.

The method used for reducing these ruthenium compounds includes a catalytic reduction method with hydrogen, carbon monoxide or the like, or a chemical reduction method with formalin, sodium borohydride, potassium borohydride, hydrazine or the like. Among others, a catalytic reduction with hydrogen and a chemical reduction with sodium borohydride are preferred. In the case of the catalytic reduction with hydrogen, the ruthenium compounds are reduced and activated generally at a temperature of from 50 to 450° C., preferably from 100 to 400° C. When the reduction temperature is lower than 50° C., it takes a too long time for the reduction, and when it is higher than 450° C., aggregation of ruthenium may proceed, resulting in adverse effects on the activity and selectivity thereof. The reduction may be carried out in a gas phase or a liquid phase, preferably in a liquid phase. Further, in the case of the chemical reduction with sodium borohydride, the reduction temperature is preferably 100° C. or lower, more preferably from 10 to 60° C.

Further, the ruthenium to be charged at the partial hydrogenation may be a ruthenium compound which does not contain metallic ruthenium. The ruthenium compound in this case is required to be a compound such as a hydroxide which does not contain chloride ions.

When a ruthenium catalyst which does not contain metallic ruthenium is charged at the partial hydrogenation, particularly preferred is a catalyst supporting ruthenium hydroxide on a carrier prepared by loading the ruthenium compound as described above on a carrier and treating the product with an alkali such as sodium hydroxide, or a mixture of ruthenium hydroxide and a dispersant which is obtained by adding an alkali such as sodium hydroxide to a mixture containing the dispersant and the above ruthenium compound.

Furthermore, as the ruthenium compound as described above, may be used those mainly composed of ruthenium obtained by adding, to a ruthenium compound before or after reduction, other metals or metal compounds, for example, zinc, chromium, molybdenum, tungsten, manganese, cobalt, nickel, iron, copper, gold, platinum, boron, lanthanum, cerium and the like, or metal compounds of these metals. When these metals or metal compounds are used, the atomic ratio of the metal to the ruthenium atom is generally selected in the range of from 0.001 to 20. Among the metals or metal compounds as described above, zinc or a zinc compound is preferred. Zinc or a zinc compound is preferably added before or during the reduction of a ruthenium compound, and the amount to be added is preferably in the range of from 0.1 to 50% by weight in terms of zinc based on ruthenium. Further, from the viewpoint of catalytic activity and cycloolefin selectivity, the amount to be added is most preferably in the range of from 0.5 to 30% by weight in terms of zinc based on ruthenium.

A method which can be used for preparing a catalyst mainly composed of ruthenium containing such a metal or a metal compound includes, for example, (1) a method in which a ruthenium compound and another metal or metal compound are loaded on a carrier and then subjected to reduction; (2) a method in which an alkali such as sodium hydroxide is added to a solution containing a ruthenium compound and another metal or metal compound to precipitate the ruthenium compound together with the another metal or the like as an insoluble salt, which is then reduced; (3) a method in which an insoluble ruthenium compound is loaded on a carrier as necessary, and the ruthenium compound is reduced in a liquid phase containing another metal compound or the like; (4) a method in which a ruthenium compound and another metal compound are subjected to reduction treatment in a state where they are dissolved in a liquid phase; and the like.

The ruthenium catalyst may be used by loading it on a carrier. Specific examples of the carrier include, but are not limited to, oxides, complex oxides, hydroxides and hardly water-soluble metal salts of a metal such as magnesium, aluminum, silicon, calcium, titanium, vanadium, chromium, manganese, cobalt, iron, nickel, copper, zinc, zirconium, hafnium, tungsten and boron; compounds and mixtures prepared by chemically or physically combining two or more of the above compounds; and the like.

Among others, zirconium oxide and zirconium hydroxide are preferred, and particularly preferred is zirconium oxide in that it has excellent physical stability of the specific surface area under reaction conditions. The zirconium oxide preferably has an average particle size of from 0.05 to 30 μm, more preferably from 0.05 to 10 μm. It preferably has a specific surface area of from 20 to 200 m$^2$/g and an average pore size of from 1 to 50 nm. A method for loading ruthenium on such a carrier is not particularly limited, but includes several disclosed methods such as an absorption method, an ion-exchange method, an immersion method, a coprecipitation method and solidification by drying.

The amount of usage of a carrier is, but not limited to, generally from 1 to 1,000 times by mass of ruthenium. In particular, when zirconium oxide is used as a carrier, it is preferably used in an amount from 1 to 200 times by mass of ruthenium, more preferably from 2 to 20 times by mass of ruthenium.

Further, when ruthenium is used as it is with no support by a carrier, oxides, complex oxides, hydroxides and hardly water-soluble metal salts of a metal such as magnesium, aluminum, silicon, calcium, titanium, vanadium, chromium, manganese, cobalt, iron, nickel, copper, zinc, zirconium, hafnium, tungsten, barium and boron; compounds and mixtures prepared by chemically or physically combining two or more of the above compounds; and the like are preferably used as dispersants.

The ruthenium catalyst preferably has an average crystallite size of 20 nm or less. The average crystallite size in this range is preferred because it provides a suitable surface area of the ruthenium catalyst so that the active sites are sufficiently present and the catalytic activity is improved. The average crystallite size is determined using the Scherrer equation from the broadening of the diffraction line width obtained by an X-ray diffraction method of the ruthenium catalyst to be used. Specifically, the CuKα radiation is used as the X-ray source to determine the average crystallite size from the broadening of the diffraction line having a maximum near a diffraction angle (2θ) of 44°. In addition, the lower limit of the average crystallite size is theoretically larger than the crystalline unit, and it is actually 1 nm or more.

The reaction system of the present invention requires water, the amount of which is different by the reaction form and is preferably from 0.5 to 20 times by mass of the raw material monocyclic aromatic hydrocarbon to be used. By using water in an amount of this range, the cycloolefin selectivity can be maintained without increasing the size of a reactor. More preferably, the amount of water is from 1 to 10 times by mass of the raw material monocyclic aromatic hydrocarbon to be used. In any case, water must be present in the reaction system in an amount enough to form a state in which a liquid organic matter phase (oil phase) containing a raw material or a product as a main component is phase-separated from a water phase containing water as a main component, that is, a two-liquid-phase state composed of an oil phase and a water phase. As described herein "a main component" refers to a component whose content is the highest in terms of the number of moles among the components of the liquid phase of interest.

In addition, the pH in the water phase is preferably acidic or neutral, i.e., 7 or less.

Furthermore, in the present invention, it is necessary that a metal sulfate should be present. The metal sulfate should be present in the water phase in a state where at least a part or all of the same is dissolved therein. Specific examples of the metal sulfate to be present in the reaction system include sulfates of zinc, iron, nickel, cadmium, gallium, indium, magnesium, aluminum, chromium, manganese, cobalt and copper. Two or more of these sulfates may be used in combination, and double salts containing these metal sulfates may also be used. In particular, zinc sulfate is preferably used as the metal sulfate. The metal sulfate is preferably used in an amount such that the concentration of the same in the water phase is from $1 \times 10^{-5}$ to 5.0 mol/l. When a metal salt containing zinc sulfate is used, the concentration of the same in the water phase is preferably from $1\times10^{-3}$ to 2.0 mol/l, more preferably from 0.1 to 1.0 mol/l.

In addition, the following metal salts may be present in the reaction system of the present invention as in conventional methods. Examples of the types of the metal salts include nitrates, oxides, hydroxides, acetates, phosphates and the like of group 1 metals in the periodic table such as lithium, sodium and potassium, group 2 metals in the periodic table such as magnesium and calcium (the group numbers are in accordance with the notation of a revised edition (1989) of IUPAC Inorganic Chemistry Nomenclature), and metals such as zinc, manganese, cobalt, copper, cadmium, lead, arsenic, iron, gallium, germanium, vanadium, chromium, silver, gold, platinum, nickel, palladium, barium, aluminum and boron. Two or more of these metal salts may be chemically or physically mixed for use in the reaction system of the present invention. Among others, zinc salts such as zinc hydroxide and zinc oxide are preferred. Particularly preferred are double salts containing zinc hydroxide, for example, a double salt represented by the general formula: $(ZnSO_4)_m \cdot (Zn(OH)_2)_n$ wherein m:n=1:0.01-100.

However, metal chlorides are not preferred because when they are present in the water phase, the chloride ion concentration in water increases, adversely affecting the long-term performance of the catalyst.

The amount of usage of the metal salt is not particularly limited so long as it maintains the water phase in an acidic or neutral condition and is usually in the range of from $1\times10^{-5}$ to $1\times10^5$ times by mass of the ruthenium to be used. The metal salt may be present anywhere in the reaction system, and all of the metal salt is not necessarily dissolved in the water phase.

A first feature of the present invention is that, when a cycloolefin is produced by partially hydrogenating a monocyclic aromatic hydrocarbon with hydrogen in the presence of a ruthenium catalyst, water, and a metal sulfate, the concentration of chloride ions dissolved in the water in which the catalyst is present is reduced to 300 wt ppm or less, preferably 200 wt ppm or less, and more preferably 100 wt ppm or less. The chloride ion concentration is preferably maintained in 90% or more of the production steps, more preferably in 95% or more of the productions steps, and most preferably in all of the productions steps.

In the present invention, the chloride ion concentration refers to the sum of all the concentrations of chloride which is present in the form of chloride atoms and ions including free residual chloride which is present, maintaining the state of equilibrium of chloride $Cl_2$, hypochlorous acid HClO, and hypochlorite $ClO^-$; combined residual chloride which is present in the form of chloramine produced by the reaction of chloride with ammonium ions present in water; and chloride ions present in the form of $Cl^-$.

If the chloride ion concentration is higher than 300 wt ppm, the decrease in the activity and cycloolefin selectivity in the case where the ruthenium catalyst is used for a long period of time would be large. It is not necessarily clear why both the reaction activity and cycloolefin selectivity of the ruthenium catalyst are decreased by the chloride ions dissolved in water, but the following reasons are conceivable. When chloride ions are present in water, ruthenium dissolves into the water and undergoes rereduction, which promotes the sintering of ruthenium, causing the decrease in the activity of the catalyst. The interaction between ruthenium and a metal or a metal compound present together with ruthenium changes at the same time. The cycloolefin selectivity also decreases presumably because the metal or the metal compound has an important role on the cycloolefin selectivity.

The chloride ion concentration dissolved in the water in which the ruthenium catalyst is present can be reduced to 300 wt ppm or less by controlling the chloride ion concentration of each constituent present in the water phase. Specifically, the chloride ion concentration dissolved in water can be reduced to 300 wt ppm or less by controlling the concentration of chloride ions contained in each of water, a catalyst, a dispersant, a metal sulfate, a metal salt, a monocyclic aromatic hydrocarbon, and hydrogen to be supplied to the reaction system to a certain level or less.

According to the present invention, the chloride ion content in the water to be supplied to the reaction is preferably 20 wt ppm or less, more preferably 10 wt ppm or less, and most preferably 5 wt ppm or less. Examples of the method for adjusting the chloride ion content in water in the above range include treatment with ion-exchange resins, purification by distillation, and the like.

The electric conductivity in the water described above is preferably 0.5 µS/cm or less, more preferably 0.3 µS/cm or less, when it is indicated by the electric conductivity which is generally used. By reducing the chloride ion concentration in the water to be supplied to 20 wt ppm or less, the degradation of the activity and the decrease in the cycloolefin selectivity of the catalyst hardly occur even when the catalyst is used in the reaction for a long period of time.

The chloride ions in the ruthenium catalyst are considered to directly affect the catalyst degradation when the catalyst is used for a long period of time because the chloride ions are present in the vicinity of ruthenium. As a result of the investigation by the present inventors, it is found that the chloride ion content in the catalyst which hardly affects the catalyst degradation is 400 wt ppm or less, preferably 100 ppm or less. Further, the chloride ion content based on ruthenium in the catalyst is 500 wt ppm or less. Examples of the method for adjusting the chloride ion content include a method in which a ruthenium catalyst is washed with distilled water before or after the reduction for preparing the catalyst until the chloride concentration in the catalyst decreases to 400 wt ppm or less; and a method, when a mixture of ruthenium hydroxide and a dispersant is used as a catalyst, ruthenium hydroxide is suspended in an aqueous sodium hydroxide solution, and the resulting mixture is stirred for several hours and then filtered, the stirring and filtration being carried out several times before the mixture is further washed with distilled water.

The chloride ion content in oxides, complex oxides, hydroxides and hardly water-soluble metal salts of magnesium, aluminum, silicon, calcium, titanium, vanadium, chromium, manganese, cobalt, iron, nickel, copper, zinc, zirconium, hafnium, tungsten or the like; compounds or mixtures prepared by chemically or physically combining two or more of the above compounds; or the like used as carriers or dispersants is preferably 200 wt ppm or less, more preferably 100 wt ppm or less. Zirconium oxide or zirconium hydroxide is preferred as a carrier or a dispersant. The chloride ion content in these compounds is preferably 100 wt ppm or less, more preferably 50 wt ppm or less. Examples of the method for adjusting the chloride ion content in these compounds include a method in which a suspension of each of these compounds in distilled water is heat-treated at a temperature of 80° C. or higher and filtrated, the heat treatment and filtration being repeated.

According to the present invention, it is required that a metal sulfate be present in water. The chloride ion concentration in the metal sulfate is preferably 10 wt ppm or less, more preferably 5 wt ppm or less. Examples of the method for adjusting the chloride ion content include a method in which purification by the recrystallization of the metal sulfate in distilled water or ethanol as a solvent is repeated.

The concentration of chloride ions in the monocyclic aromatic hydrocarbon used in the present invention is preferably 10 wt ppm or less, more preferably 1 wt ppm or less. By controlling chloride ions in the monocyclic aromatic hydrocarbons to 10 wt ppm or less, the supply of chloride ions can be suppressed even in the case where the catalyst is used for a long period of time, thereby capable of maintaining the catalyst performance for a long period of time. Examples of the method for adjusting the chloride ion content include a method in which the monocyclic aromatic hydrocarbon is mixed and stirred with ion-exchanged water under high-speed agitation and then oil is separated from the mixture to recover benzene, these operations being repeated.

The hydrogen to be used in the present invention is also affected by chloride ions. Therefore, the chloride ion concentration is preferably 1 mg-Cl/Nm$^3$-H$_2$ or less, more preferably 0.5 mg-Cl/Nm$^3$-H$_2$ or less. Here, N (normal) means that the unit is based on the gas in the standard state. Examples of the method for adjusting the chloride ion content include a method in which hydrogen is passed through a column in which potassium hydroxide pellets or sodium hydroxide pellets are filled; a method of blowing hydrogen gas in the form of fine bubbles into an aqueous sodium hydroxide solution or distilled water under agitation; and a method of passing hydrogen through a trap cooled with liquid nitrogen.

When cycloolefins are produced continuously, it is possible to prevent the increase in the chloride ion concentration to a level exceeding 300 wt ppm during the continuous reaction and maintain the catalyst performance by keeping the chloride ion concentration in the raw material monocyclic aromatic hydrocarbon, the chloride ion concentration in hydrogen, and the chloride ion concentration in water to be supplied to the reaction at the respective values as described above.

Even if the chloride ion concentration in the monocyclic aromatic hydrocarbon, the chloride ion concentration in hydrogen, and the chloride ion concentration in water to be supplied to the reaction are the same, the rate of the increase in the chloride ion concentration with time in the water in which the catalyst is present differs by the method of preparing the catalyst. This is because the chloride ion concentration in the water in which the catalyst is present is closely related with the chloride ion concentration on the catalyst and with a physical state of ruthenium which changes with the difference of the method of preparing the catalyst such as the crystallite size or the surface area of ruthenium on the catalyst. Therefore, although it is difficult to define the chloride ion concentration in the water in which the catalyst is present in the continuous reaction, as a criterion, the chloride ion concentration preferably does not exceed 300 wt ppm for 500 hours after starting the partial hydrogenation, in consideration of the industrial production of cycloolefins.

Liquid phase reaction is a preferred reaction. The reaction system may typically include a continuous or a batchwise reaction by a liquid phase suspension method using a reaction vessel or two or more reaction vessels, but it may include a fixed-phase mode.

A second feature of the present invention is to regenerate a part or all of the catalyst and then reuse the regenerated catalyst.

It is not necessarily clear why the decrease in the catalytic activity and cycloolefin selectivity can be suppressed by regenerating a part or all of the catalyst in addition to controlling the chloride ion concentration in the water in which the catalyst is present so that it does not exceed 300 wt ppm, but the followings are assumed.

First, a low chloride ion concentration in the water in which the catalyst is present provides a sintering suppression effect of ruthenium as described above. The sintering suppression effect can maintain the regenerated performance of the catalyst and can also maintain the activity and cycloolefin selectivity after the catalyst is regenerated.

The followings are also assumed. A low chloride ion concentration may enhance the interaction between hydrogen and ruthenium and that between a metal ion derived from a metal sulfate such as an ion of zinc and ruthenium. This may increase the number of hydrogen atoms which are strongly bonded to ruthenium and decrease the catalytic activity. In addition, the amount of zinc ions absorbed on ruthenium may increase and part of the zinc ions may be reduced to a metal state to poison ruthenium, resulting in the decrease in the catalytic activity and cycloolefin selectivity. Therefore, the regeneration of the catalyst may be able to remove the excess amount of hydrogen and metal ions absorbed on ruthenium and thereby may be able to suppress the decrease in the catalytic activity and cycloolefin selectivity.

The amount of the catalyst to be regenerated may be a part or all of the catalyst and may be appropriately selected according to a production line. Regeneration of the catalyst may be performed by a batchwise method or a continuous method.

It is preferred to regenerate all of the catalyst when the reaction is performed batchwise in that the activity and cycloolefin selectivity of the regenerated catalyst can be easily controlled by grasping the relationship between the regeneration conditions and the activity and cycloolefin selectivity of the regenerated catalyst by a basic experiment. On the other hand, it will be possible to obtain the following effect by regenerating a part of the catalyst. That is, when a part of the catalyst is regenerated, a mixture of a regenerated catalyst and a catalyst which has not undergone regeneration will be reused. This means that the mixture contains a catalyst on which an optimum amount of hydrogen and metal ions are absorbed in terms of the catalytic activity and cycloolefin selectivity. Therefore, it is preferred to regenerate a part of the catalyst in that a regeneration treatment which is a treatment involving abrupt change on ruthenium can be performed relatively mildly and the activity and cycloolefin selectivity can be maintained in a good balanced in a long-term use of the catalyst.

When cycloolefins are produced by a batchwise reaction, a part of the catalyst is preferably from 5% by weight to 80% by weight of the catalyst for use in the reaction, more preferably from 10% by weight to 60% by weight. Further, it is practical to change the amount of the catalyst to be regenerated in the continuous reaction depending on the degree of the decrease in the catalyst performance per hour. For example, 5% to 80% of the total catalyst is regenerated in 24 hours, more preferably from 10% by weight to 60% by weight.

A method for removing a part or all of the catalyst from the continuous reaction to subject it to regeneration treatment and returning the resulting regenerated catalyst back to the partial hydrogenation reactor is not particularly limited. For example, in the case of a continuous reaction, the method may include a method in which the continuous reaction is suspended; an oil phase is removed; all of the liquid phase containing the catalyst is subjected to regeneration treatment; and then partial hydrogenation is started again, or a method in which a part of the liquid phase containing the catalyst is removed, subjected to regeneration treatment, and recharged to the partial hydrogenation reactor without stopping the continuous reaction. The apparatus and the operating method for performing continuous removal, regeneration treatment, and refilling include a method and an apparatus comprising a partial hydrogenation reactor, a jacketed cooler, and a jacketed reactivation treater as disclosed in JP-A-2001-26556.

The regeneration method includes known methods such as (1) a method of bringing the catalyst into contact with oxygen in a liquid phase, and (2) a method of maintaining the catalyst at a hydrogen partial pressure lower than that at the hydrogenation and a temperature not lower than the temperature lower by 50° C. than the hydrogenation temperature.

In the first method as described above which is a catalyst regeneration method for bringing the catalyst into contact with oxygen in a liquid phase, the state of the liquid phase may be a state in which the ruthenium catalyst is dispersed in a suitable liquid to form a slurry, wherein the amount of the liquid may be small, but at least the surface of the catalyst should be covered with the liquid. The liquid used here may be any liquid so long as it has no adverse influence on the catalyst or the carrier thereof, preferably water.

When the catalyst is brought into contact with oxygen in the liquid phase, the oxygen source which can be used includes oxygen gas, a gas containing molecular oxygen such as air, or a compound capable of generating nascent oxygen such as hydrogen peroxide. Oxygen gas is preferably used as it is or after being diluted with a suitable inert gas because such an operation is easy.

The oxygen concentration of the liquid phase is generally from $1 \times 10^{-7}$ to 1 Nml/ml, preferably from $1 \times 10^{-5}$ to 0.1 Nml/ml, in terms of oxygen gas in the standard state. When the oxygen concentration is in this range, the treatment can be completed in a relatively short period of time, and it is possible to prevent an irreversible change by a sudden oxidation of ruthenium on the surface of the catalyst from occurring.

Oxygen may be directly supplied to the liquid phase in a slurry state. The most preferred method of supplying oxygen is to disperse the ruthenium catalyst in water and supply an oxygen-containing gas to the resulting dispersion. This method is preferred because operation is simple.

The operations for recovering the activity of the ruthenium catalyst can be carried out under any conditions, such as under reduced pressure or at atmospheric pressure or under increased pressure. Pressurizing may be conducted for increasing the oxygen concentration of the liquid phase. The operating temperature at which the catalyst is brought into contact with oxygen is from 0 to 300° C., preferably from 30 to 200° C., more preferably from 50 to 150° C. The operating time may be properly determined depending on the degree of decrease in activity of a catalyst to be treated and the desired degree of recovery of the activity, and is usually several minutes to several days.

The second regeneration method of maintaining the catalyst at a hydrogen partial pressure lower than that at the hydrogenation and a temperature not lower than the temperature lower by 50° C. than the hydrogenation temperature can be carried out in either a gas phase or a liquid phase. The hydrogen partial pressure may be any pressure so long as it is lower than a hydrogen partial pressure at the hydrogenation. It, however, is preferably one-half or less of the hydrogen partial pressure at the hydrogenation, more preferably zero or a pressure close to zero because when the difference between the two hydrogen partial pressures is not sufficient, the recovery of the activity requires a long period of time in some cases. The operating temperature at which the catalyst is maintained is not lower than the temperature lower by 50° C. than the hydrogenation temperature, preferably not lower than the temperature lower by 40° C. than the hydrogenation temperature, more preferably not lower than the temperature lower by 30° C. than the hydrogenation temperature. The operating temperature may be higher than the hydrogenation temperature. However, when the temperature is too high, an irreversible change is caused in the active site of the catalyst in some cases. Therefore, it is preferable to choose the upper limit of the operating temperature which is suitable for the properties of the catalyst. In the case of metallic ruthenium fine particles to be used as a catalyst, for example, it is preferable to maintain the catalyst at a temperature not higher than 250° C., preferably not higher than 200° C., for preventing the physical change in the properties of the catalyst. On the other hand, when the operating temperature is lower than the temperature lower by 50° C. than the hydrogenation temperature, a treatment for a very long period of time may be required for recovering the activity. The maintaining time may be properly determined depending on the degree of decrease in the activity of a catalyst to be treated and the desired degree of recovery of the activity, and is usually several minutes to several days. When the two regeneration methods as described above are used in combination, either the first method or the second method may be carried out first. Preferably, the method of bringing the catalyst into contact with oxygen in a liquid phase is carried out first. For carrying out such operations for recovering the activity, it is preferable that organic substances derived from the hydrogenation and present together with the ruthenium catalyst are previously separated and removed from the ruthenium catalyst. The organic substances present together with the ruthenium catalyst refer to a monocyclic aromatic hydrocarbon as a raw material, a reaction product, a by-product, impurities, and the like.

The ruthenium catalyst whose activity has been restored is reused for reaction after being properly washed, dried and then formed into a preferred shape.

It is possible to reactivate the activity and cycloolefin selectivity of a degraded catalyst to some degree by taking out a part or all of the catalyst and carrying out only the regeneration treatment, but this reactivation is not necessarily sufficient. The decrease in the activity and cycloolefin selectivity of the catalyst can be significantly suppressed by maintaining the concentration of chloride ions dissolved in the water of the catalyst slurry to 300 wt ppm or less, in addition to the regeneration treatment of the catalyst. In addition, since the regenerated performance of the catalyst can be enhanced, it is possible to maintain a high catalytic activity and cycloolefin selectivity also after the regeneration treatment. The mechanism that the degradation of the catalyst can be suppressed by maintaining a low chloride ion concentration in addition to the regeneration treatment is not necessarily clear, but the followings are assumed. Namely, there may be a plurality of factors behind the decrease in selectivity and activity of the catalyst. When the chloride ions in the water in which the catalyst is present are reduced, the catalyst degradation due to irreversible causes which cannot be reactivated by the regeneration treatment may be suppressed. As a result, the catalyst performance can be maintained also after the regeneration treatment. Further, the regeneration of the catalyst may be able to remove the excess amount of hydrogen and metal ions absorbed on the ruthenium catalyst and thereby may be able to suppress the decrease in the catalytic activity and cycloolefin selectivity.

Moreover, the chloride ions accumulated on the catalyst can be removed from the catalyst and return to the liquid phase by the regeneration treatment. The returned chloride ions dissolve into an oil phase or into the water accompanying the oil phase and are removed out of the reaction system. As a result, the chloride ion concentration on the catalyst can be maintained at a low level, thereby suppressing the decrease in the selectivity and activity of the catalyst. Thus, a short-term as well as a long-term decrease in the selectivity and activity of the catalyst can be remarkably suppressed by keeping the chloride ion concentration low in the water containing the catalyst together with the regeneration treatment.

EXAMPLES

The present invention will now be described with reference to Examples, but the present invention is not limited to Examples so long as they do not depart from the gist of the present invention. The conversion of benzene and selectivity of cyclohexene as described in Examples below are calculated from the formulas shown below on the basis of analytical values of concentration in the experiments.

$$\text{Conversion of benzene}(\%) = \frac{\text{Number of moles of benzene consumed in reaction}}{\text{Number of moles of benzene supplied to reactor}} \times 100 \quad \text{[Formula 1]}$$

$$\text{Selectivity of cyclohexene}(\%) = \frac{\text{Number of moles of cyclohexene produced by reaction}}{\text{Number of moles of cyclohexene produced by reaction} + \text{Number of moles of cyclohexane produced by reaction}} \times 100 \quad \text{[Formula 2]}$$

The chloride ion concentration in the catalyst and that in the metal oxide used as a dispersant were measured using fluorescent X-rays (RIX-3100 manufactured by Rigaku Denki). The chloride ion concentration in metal salts was measured as an aqueous solution by the ion chromatogram (IC 7000 manufactured by Yokogawa Analytical Systems). The chloride ion concentration in the water supplied to the reaction was also measured by the ion chromatogram. The chloride ion concentration in monocyclic aromatic hydrocarbons was analyzed using a chloride microanalyzer (TS-300 type manufactured by Mitsubishi Chemical). As for the chloride ion concentration in the raw material hydrogen, the hydrogen was bubbled into an aqueous NaOH solution to allow chloride ions in the hydrogen to be absorbed in the solution. Then, the resulting solution was analyzed for the chloride ion concentration using the above-described chloride microanalyzer. The chloride ion concentration dissolved in water in the water phase containing the catalyst was analyzed using the above-described chloride microanalyzer using a liquid obtained after the filtration of the catalyst.

Example 1

In 260 ml of distilled water, was dissolved 6.5 g of ruthenium chloride hydrate (containing 40% by weight of ruthenium). To the mixture, was added a solution prepared by dissolving 0.27 g of zinc chloride in 20 ml of distilled water. To the resulting mixture, was added 20 g of a zirconium oxide powder (manufactured by Wako Pure Chemical Industries, Ltd.) whose chloride ion content was 70 wt ppm, followed by stirring so as to obtain a uniform suspension. To the resulting suspension, was added over 1 hour an aqueous solution prepared by dissolving 28.0 g of sodium borohydride in 730 ml of distilled water, while maintaining the temperature of the suspension at 30° C. or lower and cooling the aqueous sodium borohydride solution with ice. After adding the whole amount of the aqueous sodium borohydride solution, the mixture was stirred at room temperature for 1 hour and then left at rest at room temperature for 16 hours. The resulting catalyst slurry was filtered and washed with distilled water until the filtrate had a neutral pH. Further, the catalyst was suspended again in distilled water, stirred for 1 hour, and then filtered. These operations were repeated. A part of the obtained wet catalyst was dried and measured for the chloride ion concentration using fluorescent X-rays. The chloride ion concentration was found to be 180 wt ppm, and the crystallite size of ruthenium was found to be about 3 nm.

Into a tank flow reactor were charged 23 g in terms of dry mass of the above catalyst and 1,000 ml of a 22 wt % aqueous solution of zinc sulfate ($ZnSO_4 \cdot 7H_2O$, manufactured by Wako Pure Chemical Industries, Ltd.). The tank flow reactor was equipped with an oil separating tank as an attached tank and had a Teflon (registered trade mark) coating on the inner surface thereof. Subsequently, partial hydrogenation of benzene was continuously carried out at 140° C. under a hydrogen pressure of 5 MPa while feeding benzene which did not contain sulfur, thiophene, iron, and nickel at a rate of 0.8 L/Hr. At this time, water was fed so that the composition of the aqueous phase containing the catalyst in the reaction system was always kept constant, and the reaction product consisting of benzene, cyclohexene and cyclohexane was continuously taken out of the oil separating tank. The volume ratio of the water phase to the oil phase in the reactor was kept constant at 1:0.3. The zinc sulfate was used without any particular purification treatment. The chloride ion concentration in the zinc sulfate was 5 wt ppm or less. City water which was purified by distillation was used as the water for preparing the aqueous zinc sulfate solution and the water to be supplied during the continuous reaction. The chloride ion concentration of the purified water was 0.5 wt ppm. Purified benzene was obtained by repeating the operation of mixing and stirring industrially produced benzene with distilled water. The purified benzene having a chloride ion concentration of 1 wt ppm was used for the reaction. Hydrogen was purified by passing industrially produced hydrogen through a column filled with potassium hydroxide pellets. The purified hydrogen having a chloride ion concentration of 0.5 mg-Cl/$Nm^3$-$H_2$ was used for the reaction.

The results of partial hydrogenation at 500 hours after the start of the reaction showed a benzene conversion of 30% and a cyclohexene selectivity of 81%. At this time point, a small amount of the catalyst slurry was sampled and measured for the chloride ion concentration in water after filtering off the catalyst. The chloride ion concentration in water was found to be 56 wt ppm. When the continuous reaction was further allowed to proceed, the activity gradually decreased, and at 1,000 hours after the start, it was found that the benzene conversion was 24% and the cyclohexene selectivity was 83%. At 1,000 hours after the start, the feed rate of benzene was reduced to obtain a benzene conversion of 30%, and as a result it was found that the cyclohexene selectivity was 80%, which was about the same as the selectivity at 500 hours after the start. At this time point, a small amount of the catalyst slurry was sampled again and measured for the chloride ion concentration in water after filtering off the catalyst. The chloride ion concentration in water was found to be 62 wt ppm, substantially no increase in the chloride ion concentration in water having been observed.

The reaction was stopped after 1,000 hours; the oil phase was removed; and the catalyst slurry was bubbled with nitrogen gas at 20° C. for 2 hours. Subsequently, low boiling-point organic substances such as benzene, cyclohexene and cyclohexane were completely removed, and then the resulting slurry was brought into contact with nitrogen containing 7% by volume oxygen at 50° C. for 1 hour, followed by displacement thereof with nitrogen and then with hydrogen. After these operations, the catalyst slurry was raised to a temperature of 140° C. and stirred for 4 hours while maintaining the internal pressure of the system under a hydrogen atmosphere of 0.5 MPa to carry out the operation of recovering the catalytic activity, using the total quantity of the catalyst slurry. After completion of the operation, supply of hydrogen and benzene was started again to carry out the partial hydrogenation of benzene under the same conditions as described above. With regard to the results of partial hydrogenation after 24 hours from the restart of the reaction, it was found that the benzene conversion was 37% and the cyclohexene selectivity was 77%. When the flow rate of benzene was increased to reduce the benzene conversion to 30%, the cyclohexene selectivity was 79%. It was verified that the catalytic activity was recovered by the regeneration operation and the cyclohexene selectivity was close to that of the results at 500 hours after the start. The results are shown in Table 1.

Comparative Example 1

In 260 ml of distilled water, was dissolved 6.5 g of ruthenium chloride hydrate (containing 40% by weight of ruthenium). To the mixture, was added a solution prepared by dissolving 0.35 g of zinc chloride in 20 ml of distilled water. To the resulting mixture, was added 20 g of a zirconium oxide powder (manufactured by Daichi Kigenso Kagaku Kogyo Co., Ltd.) whose chloride ion content was 320 wt ppm, followed by stirring so as to obtain a uniform suspension. To the resulting suspension, was added over 1 hour an aqueous solution prepared by dissolving 28.0 g of sodium borohydride in 730 ml of distilled water, while maintaining the temperature of the suspension at 30° C. or lower and cooling the aqueous sodium borohydride solution with ice. After adding the whole amount of the aqueous sodium borohydride solution, the mixture was stirred at room temperature for 1 hour and then left at rest at room temperature for 16 hours. The resulting catalyst slurry was filtered, and the obtained wet catalyst was suspended in 300 ml of distilled water, filtered and washed once. A part of the obtained wet catalyst was dried and measured for the chloride ion concentration using fluorescent X-rays. The chloride ion concentration was found to be 430 wt ppm, and the crystallite size of ruthenium was found to be about 3.5 nm.

Partial hydrogenation of benzene was carried out continuously in the same manner as in Example 1, using 30 g in terms of dry mass of the above catalyst. However, city water was used as the water for preparing the aqueous zinc sulfate solution and the water to be supplied during the continuous reaction. The chloride ion concentration in the water was 16 wt ppm. The chloride ion concentration in the zinc sulfate was 5 wt ppm or less. The benzene industrially produced was used as it is. The chloride ion concentration in the benzene was 15 wt ppm. The hydrogen prepared by passing industrially produced hydrogen through distilled water was used. The chloride ion concentration in the hydrogen was 1.8 mg-Cl/$Nm^3$-$H_2$.

The results of partial hydrogenation at 600 hours after the start of the reaction showed a benzene conversion of 28% and a cyclohexene selectivity of 75%. At this time point, a small amount of the catalyst slurry was sampled and measured for the chloride ion concentration in water after filtering off the catalyst, and it was found to be 310 wt ppm. When the continuous reaction was further allowed to proceed, the activity greatly decreased, and at 1,000 hours after the start, it was found that the benzene conversion was 16% and the cyclohexene selectivity was 74%. At 1,000 hours after the start, the feed rate of benzene was reduced to obtain a benzene conversion of 28%, and as a result it was found that the cyclohexene selectivity was 64%, having greatly decreased from the selectivity at 500 hours after the start. A small amount of the catalyst slurry was sampled and measured for the chloride ion concentration in water after filtering off the catalyst. The chloride ion concentration in water was found to be 456 wt ppm, increase in the chloride ion concentration in water having been observed.

The reaction was stopped after 1,000 hours, and the operation of recovering the catalytic activity was carried out in the same manner as in Example 1. After completion of the operation, supply of hydrogen and benzene was started again to carry out the partial hydrogenation of benzene under the same conditions as described above. With regard to the results of partial hydrogenation after 24 hours from the restart of the reaction, it was found that the benzene conversion was 18% and the cyclohexene selectivity was 70%. When the flow rate of benzene was reduced to increase the benzene conversion to 28%, the cyclohexene selectivity was 64%. It was verified that the catalytic activity was not recovered even by performing the regeneration operation and the cyclohexene selectivity was lower than that of the results at 500 hours after the start by about 10%. The results are shown in Table 1.

Example 2

As a ruthenium catalyst, was used 8 g in terms of dry weight of a ruthenium hydride catalyst containing 7% by weight of zinc obtained by reducing ruthenium hydroxide in which zinc hydroxide was previously contained. The content of chloride ions in the catalyst was reduced to 10 wt ppm or less by suspending the catalyst in an aqueous sodium hydroxide solution and stirring the resulting suspension, followed by washing the catalyst with distilled water. The catalyst had an average crystallite size of about 6.3 nm. The continuous partial hydrogenation of benzene was carried out in the same manner as in Example 1 except that 64 g of a zirconium oxide powder (manufactured by Wako Pure Chemical Industries, Ltd.) whose chloride ion content was 70 wt ppm was used as a dispersant.

The results of partial hydrogenation at 500 hours after the start of the reaction showed a benzene conversion of 41% and a cyclohexene selectivity of 78%. At this time point, a small amount of the catalyst slurry was sampled and measured for the chloride ion concentration in water after filtering off the catalyst. The chloride ion concentration in water was found to be 54 wt ppm. When the continuous reaction was further allowed to proceed, the activity gradually decreased, and at 1,000 hours after the start, it was found that the benzene conversion was 32% and the cyclohexene selectivity was 84%. At 1,000 hours from the start, the feed rate of benzene was reduced to obtain a benzene conversion of 41%, and as a result it was found that the cyclohexene selectivity was 78%, which was about the same as the selectivity at 500 hours after the start. The catalyst slurry was again measured for the chloride ion concentration in water, and it was found to be 60 wt ppm, substantially no increase in the chloride ion concentration in water having been observed.

The reaction was stopped after 1,000 hours, and the operation of recovering the catalytic activity was carried out in the same manner as in Example 1. After completion of the operation, supply of hydrogen and benzene was started again to carry out the partial hydrogenation of benzene under the same conditions as described above. With regard to the results of partial hydrogenation after 24 hours from the restart of the reaction, it was found that the benzene conversion was 54% and the cyclohexene selectivity was 70%. When the flow rate of benzene was increased to reduce the benzene conversion to 41%, the cyclohexene selectivity was 76%. It was verified that the catalytic activity was recovered by the regeneration operation and the cyclohexene selectivity was close to that of the results at 500 hours after the start. The results are shown in Table 1.

Comparative Example 2

As a ruthenium catalyst, was used 8 g in terms of dry weight of a ruthenium hydride catalyst containing 7% by weight of zinc obtained by reducing ruthenium hydroxide in which zinc hydroxide was previously contained. The catalyst was washed with distilled water. The catalyst had a chloride ion content of 250 wt ppm and an average crystallite size of about 6.8 nm. The continuous partial hydrogenation of benzene was carried out in the same manner as in Example 1 except that 64 g of a zirconium oxide powder (manufactured by Daichi Kigenso Kagaku Kogyo Co., Ltd.) whose chloride ion content was 320 wt ppm was used as a dispersant. However, ground water was used as the water for preparing the aqueous zinc sulfate solution and the water supplied during the continuous reaction. The chloride ion concentration in the water was 23 wt ppm. The chloride ion concentration in the zinc sulfate was 5 wt ppm or less. The benzene which was industrially produced was used without purification. The chloride ion concentration in the benzene was 15 wt ppm. The hydrogen prepared by passing industrially produced hydrogen through distilled water was used. The chloride ion concentration in the hydrogen was 1.8 mg-Cl/Nm$^3$-H$_2$.

The results of partial hydrogenation at 500 hours after the start of the reaction showed a benzene conversion of 30% and a cyclohexene selectivity of 74%. At this time point, a small amount of the catalyst slurry was sampled and measured for the chloride ion concentration in water after filtering off the catalyst, and it was found to be 412 wt ppm. When the continuous reaction was further allowed to proceed, the activity greatly decreased, and at 1,000 hours after the start, it was found that the benzene conversion was 13% and the cyclohexene selectivity was 77%. At 1,000 hours from the start, the feed rate of benzene was reduced to obtain a benzene conversion of 30%, and as a result it was found that the cyclohexene selectivity was 68%, having decreased compared to the selectivity at 500 hours after the start. The catalyst slurry was measured for the chloride ion concentration in water, and it was found to be 620 wt ppm, increase in the chloride ion concentration in water having been observed.

The reaction was stopped after 1,000 hours, and the operation of recovering the catalytic activity was carried out in the same manner as in Example 1. After completion of the operation, supply of hydrogen and benzene was started again to carry out the partial hydrogenation of benzene under the same conditions as described above. With regard to the results of partial hydrogenation after 24 hours from the restart of the reaction, it was found that the benzene conversion was 17% and the cyclohexene selectivity was 75%. When the flow rate of benzene was reduced to increase the benzene conversion to 30%, the cyclohexene selectivity was 67%. It was verified that neither the catalytic activity nor the cyclohexene selectivity was not recovered even by the regeneration operation. The results are shown in Table 1.

Example 3

In 300 ml of distilled water, was dissolved 15 g of ruthenium chloride hydrate (containing 40% by weight of ruthenium). To the mixture, was added a solution prepared by dissolving 1.0 g of zinc chloride in 50 ml of distilled water. To the resulting mixture, was added 50 g of a zirconium oxide powder (manufactured by Wako Pure Chemical Industries, Ltd.) whose chloride ion content was 70 wt ppm, followed by stirring so as to obtain a uniform suspension. To the resulting suspension, was added 200 ml of a 1 N aqueous sodium hydroxide solution. After adding the whole amount of the 1 N aqueous sodium hydroxide solution, the mixture was stirred at room temperature for 1 hour and then left at rest at room temperature for 16 hours. The resulting catalyst (a mixture of ruthenium hydroxide, zinc hydroxide and zirconium oxide) was filtered and washed with distilled water until the filtrate had a neutral pH. Subsequently, the resulting catalyst was suspended again in 200 ml of a 1 N aqueous sodium hydroxide solution, stirred at 60° C. for 1 hour, filtered, and then washed with distilled water until the filtrate had a neutral pH. These operations were carried out once. A part of the obtained wet catalyst was dried and measured for the chloride ion concentration using fluorescent X-rays. The chloride ion concentration was found to be 310 wt ppm.

Into a tank flow reactor equipped with an oil separating tank as an attached tank and having a Teflon (registered trade mark) coating on the inner surface thereof, were charged 6 g in terms of dry mass of the above catalyst and 1,000 ml of a 18 wt % aqueous zinc sulfate (ZnSO$_4$.7H$_2$O) solution. Then, the mixture was subjected to liquid phase reduction with hydrogen by maintaining the mixture while stirring at 140° C. for 12 hours under a hydrogen pressure of 5 MPa. Continuous partial hydrogenation of benzene was performed in the same manner as in Example 1 except that the above catalyst slurry was used. As the water for preparing the aqueous zinc sulfate solution, the water supplied during the continuous reaction, zinc sulfate, benzene, and hydrogen, those having the same chloride ion concentrations as in Example 1 were used.

The results of partial hydrogenation at 500 hours after the start of the reaction showed a benzene conversion of 38% and a cyclohexene selectivity of 75%. At this time point, a small amount of the catalyst slurry was sampled and measured for the chloride ion concentration in water after filtering off the catalyst. The chloride ion concentration in water was found to be 153 wt ppm. When the continuous reaction was further allowed to proceed, the activity gradually decreased, and at 1,000 hours after the start, it was found that the benzene conversion was 25% and the cyclohexene selectivity was 80%. At 1,000 hours after the start, the feed rate of benzene was reduced to obtain a benzene conversion of 38%, and as a result it was found that the cyclohexene selectivity was 73%, which was about the same as the selectivity at 500 hours after the start. The catalyst slurry was again measured for the chloride ion concentration in water, and it was found to be 145 wt ppm, no increase in the chloride ion concentration in water having been observed.

The reaction was stopped after 1,000 hours, and the operation of recovering the catalytic activity was carried out in the same manner as in Example 1. After completion of the operation, supply of hydrogen and benzene was started again to carry out the partial hydrogenation of benzene under the same conditions as described above. With regard to the results of partial hydrogenation after 24 hours from the restart of the reaction, it was found that the benzene conversion was 48% and the cyclohexene selectivity was 69%. When the flow rate of benzene was increased to reduce the benzene conversion to 38%, the cyclohexene selectivity was 73%. It was verified that the catalytic activity was recovered by the regeneration operation and the cyclohexene selectivity was close to that of the results at 500 hours after the start. The results are shown in Table 1.

Comparative Example 3

In 300 ml of distilled water, was dissolved 15 g of ruthenium chloride hydrate (containing 40% by weight of ruthenium). To the mixture, was added a solution prepared by dissolving 1.0 g of zinc chloride in 50 ml of distilled water. To the resulting mixture, was added 50 g of a zirconium oxide powder (manufactured by Daichi Kigenso Kagaku Kogyo Co., Ltd.) whose chloride ion content was 320 wt ppm, followed by stirring so as to obtain a uniform suspension. To the resulting suspension, was added 200 ml of a 1 N aqueous sodium hydroxide solution. After adding the whole amount of the 1 N aqueous sodium hydroxide solution, the mixture was stirred at room temperature for 1 hour and then left at rest at room temperature for 16 hours. The resulting catalyst (a mixture of ruthenium hydroxide, zinc hydroxide and zirconium oxide) was filtered, and the obtained wet catalyst was suspended in 500 ml of distilled water, stirred at room temperature for 10 minutes, filtered, and washed once. A part of the obtained wet catalyst was dried and measured for the chloride ion concentration using fluorescent X-rays, and it was found to be 570 wt ppm.

Into a tank flow reactor equipped with an oil separating tank as an attached tank and having a Teflon (registered trade mark) coating on the inner surface thereof, were charged 6 g in terms of dry mass of the above catalyst and 1,000 ml of a 18 wt % aqueous zinc sulfate ($ZnSO_4 \cdot 7H_2O$) solution. Then, the mixture was subjected to liquid phase reduction with hydrogen by maintaining the mixture while stirring at 140° C. for 12 hours under a hydrogen pressure of 5 MPa. Continuous partial hydrogenation of benzene was performed in the same manner as in Example 1 except that the above catalyst slurry was used. However, ground water was used as the water for preparing the aqueous zinc sulfate solution and the water supplied during the continuous reaction. The chloride ion concentration in the water was 23 wt ppm. The chloride ion concentration in the zinc sulfate was 5 wt ppm or less. The benzene which was industrially produced was used without purification. The chloride ion concentration in the benzene was 15 wt ppm. The hydrogen which was industrially produced was used without purification. The chloride ion concentration in the hydrogen was 2.1 $mg\text{-}Cl/Nm^3\text{-}H_2$.

The results of partial hydrogenation at 500 hours after the start of the reaction showed a benzene conversion of 33% and a cyclohexene selectivity of 73%. At this time point, a small amount of the catalyst slurry was sampled and measured for the chloride ion concentration in water after filtering off the catalyst, and it was found to be 320 wt ppm. When the continuous reaction was further allowed to proceed, the activity greatly decreased, and at 1,000 hours from the start, it was found that the benzene conversion was 16% and the cyclohexene selectivity was 75%. At 1,000 hours after the start, the feed rate of benzene was reduced to obtain a benzene conversion of 33%, and as a result it was found that the cyclohexene selectivity was 69%, having greatly decreased from the selectivity at 500 hours after the start. The catalyst slurry was measured for the chloride ion concentration in water, and it was found to be 620 wt ppm, increase in the chloride ion concentration in water having been observed.

The reaction was stopped after 1,000 hours, and the operation of recovering the catalytic activity was carried out in the same manner as in Example 1. After completion of the operation, supply of hydrogen and benzene was started again to carry out the partial hydrogenation of benzene under the same conditions as described above. With regard to the results of partial hydrogenation after 24 hours from the restart of the reaction, it was found that the benzene conversion was 21% and the cyclohexene selectivity was 71%. When the flow rate of benzene was reduced to increase the benzene conversion to 33%, the cyclohexene selectivity was 67%. It was verified that neither the catalytic activity nor the cyclohexene selectivity was recovered even by the regeneration operation. The results are shown in Table 1.

TABLE 1

|  |  | Ex. 1 | Comp. Ex. 1 | Ex. 2 | Comp. Ex. 2 | Ex. 3 | Comp. Ex. 3 |
|---|---|---|---|---|---|---|---|
| Catalyst raw material |  | Ruthenium chloride hydrate Zinc chloride | Ruthenium chloride hydrate Zinc chloride | Ruthenium hydride catalyst containing 7% of zinc | Ruthenium hydride catalyst containing 7% of zinc | Ruthenium chloride hydrate Zinc chloride | Ruthenium chloride hydrate Zinc chloride |
| | Chloride ion concentration (wt ppm) | — | — | ≦10 | 250 | — | — |
| Chloride ion concentration (wt ppm) | Zirconium oxide | 70 | 320 | 70 | 320 | 70 | 320 |
| | Ruthenium catalyst | 180 | 430 | — | — | 310 | 570 |
| | Water supplied | 0.5 | 16 | 0.5 | 23 | 0.5 | 23 |
| | Zinc sulfate | ≦5 | ≦5 | ≦5 | ≦5 | ≦5 | ≦5 |
| | Benzene | 1 | 15 | 1 | 15 | 1 | 15 |
| | Hydrogen | 0.5 | 1.8 | 0.5 | 1.8 | 0.5 | 2.1 |
| Benzene conversion (%) | After 500 hours | 30 | 28 | 41 | 30 | 38 | 33 |
| | After 1,000 hours | 24 | 16 | 32 | 13 | 25 | 16 |
| | After regeneration | 37 | 18 | 54 | 17 | 48 | 20 |
| Cyclohexene selectivity (%) | After 500 hours | 81 | 75 | 78 | 74 | 75 | 73 |
| | After 1,000 hours | 80 | 64 | 78 | 68 | 73 | 69 |
| | After regeneration | 79 | 64 | 76 | 67 | 73 | 67 |

Example 4

As a laboratory equipment for continuous reaction, was used a laboratory equipment equipped with a reactor comprising a 4-liter stainless steel autoclave having a settling zone capable of separating oil from water in the reactor; a cooling tank for continuously cooling a catalyst slurry which is taken out; and a regeneration tank for carrying out regeneration treatment in which the cooled catalyst slurry is brought into contact with oxygen-containing nitrogen. The inner surfaces of the reactor, the cooling tank, and the regeneration tank were coated with fluoropolymer resin.

Into the reactor, was charged a catalyst slurry prepared by using 40 g in terms of dry mass of the same ruthenium catalyst as prepared in Example 1, 300 g of zinc sulfate ($ZnSO_4 \cdot 7H_2O$, manufactured by Wako Pure Chemical Industries, Ltd.), and 2,000 ml of distilled water. Then, into the reactor was supplied benzene containing no catalyst-poisoning substance such as sulfur at a rate of 2 L/Hr at 140° C. under a hydrogen pressure of 5 MPa to continuously perform the partial hydrogenation of benzene. At this time, the following operations were carried out. The catalyst slurry was continuously taken out at such a flow rate that 25% of the total quantity of the catalyst slurry was taken out from the reaction system in 24 hours. The catalyst slurry which was taken out was cooled to 70 to 90° C. in the cooling tank, brought into contact with nitrogen containing 7% of oxygen for 1 hour, and continuously returned back to the reactor. Further, the volume ratio of the water phase to the oil phase in the reactor was kept constant at 1:0.5 by adjusting water supply. Here, the water used for preparing the catalyst slurry, the water supplied during the continuous reaction, benzene, and hydrogen were the same as those used in Example 1. The chloride ion concentration in water was 0.5 wt ppm; the chloride ion concentration in zinc sulfate was 5 wt ppm or less; the chloride ion concentration in benzene was 1 wt ppm; and the chloride ion concentration in hydrogen was 0.5 mg-Cl/$Nm^3$-$H_2$.

The results of partial hydrogenation at 1,000 hours after the start of the reaction showed a benzene conversion of 40% and a cyclohexene selectivity of 75%. Further, the results of the reaction at 100 hours from the start of the reaction and thereafter were very stable. The chloride ion concentration in water of the catalyst slurry was 40 wt ppm.

Comparative Example 4

The reaction was carried out in the same manner as in Example 4 except that the operation of taking out the catalyst slurry in the continuous reaction to subject it to regeneration treatment was not carried out.

Decrease in the results (activity and cyclohexene selectivity) of the partial hydrogenation was observed even at 100 hours after the start of the reaction. The results of the reaction at 1,000 hours after the start of the reaction showed a benzene conversion of 24% and a cyclohexene selectivity of 76%. When the feed rate of benzene was reduced to increase the benzene conversion to 40%, the cyclohexene selectivity was 66%, showing the decrease in both activity and selectivity compared to those in Example 4 in which regeneration treatment was performed. The chloride ion concentration in water of the catalyst slurry was 60 wt ppm.

Comparative Example 5

A catalyst prepared in Comparative Example 1 was used. The water used for preparing the catalyst slurry, the water supplied during the continuous reaction, benzene, and hydrogen were the same as those used in Comparative example 1. The chloride ion concentration in water was 16 wt ppm. The continuous reaction was carried out in the manner as in Example 4 while carrying out operations of continuously taking out the catalyst slurry, regenerating it, and returning the regenerated catalyst slurry back to the reactor, except that the chloride ion concentration in zinc sulfate was 5 wt ppm or less; the chloride ion concentration in benzene was 15 wt ppm; and the chloride ion concentration in hydrogen was 1.8 mg-Cl/$Nm^3$-$H_2$.

Decrease in the results of the partial hydrogenation was observed even at 100 hours after the start of the reaction. The results of the reaction at 1,000 hours after the start of the reaction showed a benzene conversion of 38% and a cyclohexene selectivity of 69%. When the feed rate of benzene was reduced to increase the benzene conversion to 40%, the cyclohexene selectivity was 68%. The chloride ion concentration in water of the catalyst slurry was 480 wt ppm. Both activity and selectivity were lower than those in Example 4 in which the chloride ion concentration is low.

INDUSTRIAL APPLICABILITY

According to the present invention, the catalyst can be maintained in the state where it has a high activity and high selectivity for a long period of time, so that long-term efficient production of cycloolefin can be achieved by minimizing the number of replacement operations of the catalyst and suppressing the decrease in cycloolefin selectivity. Thus, the present invention has high applicability as a method for producing cycloolefins.

The invention claimed is:

1. A method for producing a cycloolefin continuously comprising:
   partially hydrogenating a monocyclic aromatic hydrocarbon with hydrogen in the presence of a ruthenium catalyst, water, and a metal sulfate, wherein the concentration of chloride ions dissolved in the water in which the catalyst is present is 300 wt ppm or less at any time after starting the partial hydrogenation and up to 500 hours;
   regenerating the catalyst or a part thereof; and
   reusing the regenerated catalyst; wherein
   (1) the ruthenium catalyst is a catalyst comprising a carrier and/or a dispersant, and the concentration of chloride ions contained in the carrier and/or the dispersant is 200 wt ppm or less;
   (2) the concentration of chloride ions contained in the monocyclic aromatic hydrocarbon is 10 wt ppm or less;
   (3) the concentration of chloride ions contained in the hydrogen is 1 mg-Cl/$Nm^3$-$H_2$ or less (wherein N (normal) means that the unit is based on the gas in the standard state);
   (4) the concentration of chloride ions contained in water provided for the partial hydrogenation is 20 wt ppm or less;
   (5) the concentration of chloride ions in the catalyst is 400 wt ppm or less;
   (6) the concentration of chloride ions in the metal sulfate is 10 wt ppm or less.

2. The method for producing a cycloolefin continuously according to claim 1, wherein the concentration of chloride ions dissolved in the water in which the catalyst is present is 200 wt ppm or less at any time after starting the partial hydrogenation and up to 500 hours; wherein
   (1) the ruthenium catalyst is a catalyst comprising a carrier and/or a dispersant, and the concentration of chloride ions contained in the carrier and/or the dispersant is 100 wt ppm or less;
   (2) the concentration of chloride ions contained in the monocyclic aromatic hydrocarbon is 1 wt ppm or less;

(3) the concentration of chloride ions contained in the hydrogen is 0.5 mg-Cl/Nm$^3$-H$_2$ or less (wherein N (normal) means that the unit is based on the gas in the standard state);
(4) the concentration of chloride ions contained in water provided for the partial hydrogenation is 10 wt ppm or less;
(5) the concentration of chloride ions in the catalyst is 400 wt ppm or less;
(6) the concentration of chloride ions in the metal sulfate is 5 wt ppm or less.

3. The method for producing a cycloolefin according to claim 1, wherein the metal sulfate comprises zinc sulfate.

4. The method for producing a cycloolefin according to claim 1, wherein the ruthenium catalyst comprises zirconium oxide as a carrier and/or a dispersant, and the concentration of chloride ions contained in the zirconium oxide is 100 wt ppm or less.

5. The method for producing a cycloolefin according to claim 2, wherein the metal sulfate comprises zinc sulfate.

6. The method for producing a cycloolefin according to claim 2, wherein the ruthenium catalyst comprises zirconium oxide as a carrier and/or a dispersant, and the concentration of chloride ions contained in the zirconium oxide is 100 wt ppm or less.

* * * * *

UNITED STATES PATENT AND TRADEMARK OFFICE
CERTIFICATE OF CORRECTION

| | | |
|---|---|---|
| PATENT NO. | : 7,947,859 B2 | Page 1 of 1 |
| APPLICATION NO. | : 11/912575 | |
| DATED | : May 24, 2011 | |
| INVENTOR(S) | : M. Konishi et al. | |

It is certified that error appears in the above-identified patent and that said Letters Patent is hereby corrected as shown below:

On the Title page, (56) References Cited, Foreign Patent Documents,
change "CN    87116190    9/1998" to --TW    87116190    9/1998--;

On the Title page, (56) References Cited, Foreign Patent Documents,
change "CN    403676    9/2000" to --TW    403676    9/2000--;

On the Title page, (56) References Cited, Foreign Patent Documents,
change "CN    460435    10/2001" to --TW    460435    10/2001--.

Signed and Sealed this

Thirteenth Day of September, 2011

David J. Kappos
*Director of the United States Patent and Trademark Office*